US011191886B2

(12) United States Patent
Karimov et al.

(10) Patent No.: US 11,191,886 B2
(45) Date of Patent: Dec. 7, 2021

(54) MOTION-ASSISTED SYSTEMS, DEVICES AND METHODS FOR MINIMIZING OBSTRUCTION OF MEDICAL DEVICES

(71) Applicant: THE CLEVELAND CLINIC FOUNDATION, Cleveland, OH (US)

(72) Inventors: Jamshid Karimov, Cleveland Hts., OH (US); Kiyotaka Fukamachi, Mayfield Hts., OH (US); Ray Dessoffy, Parma, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 473 days.

(21) Appl. No.: 15/910,399

(22) Filed: Mar. 2, 2018

(65) Prior Publication Data

US 2018/0185557 A1 Jul. 5, 2018

Related U.S. Application Data

(63) Continuation-in-part of application No. 14/301,770, filed on Jun. 11, 2014, now Pat. No. 10,391,285.

(Continued)

(51) Int. Cl.
*A61M 1/00* (2006.01)
*A61M 1/04* (2006.01)
(Continued)

(52) U.S. Cl.
CPC .............. *A61M 1/842* (2021.05); *A61M 1/04* (2013.01); *A61M 25/00* (2013.01); *A61M 25/02* (2013.01);
(Continued)

(58) Field of Classification Search
CPC ...... A61M 1/0082; A61M 25/00; A61M 1/04; A61M 25/02; A61M 2210/101;
(Continued)

(56) References Cited

U.S. PATENT DOCUMENTS 3,159,384 A    12/1964   Davis
3,165,299 A *  1/1965   Balamuth ............. B01F 11/025
                                                    366/118

(Continued)

FOREIGN PATENT DOCUMENTS

GB          969801 A  *  9/1964  .......... B08B 9/0433

*Primary Examiner* — Adam Marcetich
(74) *Attorney, Agent, or Firm* — Tarolli, Sundheim, Covell & Tummino LLP

(57) ABSTRACT

A device for minimizing obstruction in a medical device that carries fluids includes a housing defining a channel configured to receive and secure a section of the medical device such that the section of the medical device extends coaxially with a central longitudinal axis of the channel. The device also includes components supported in the housing, including a motor, wherein the components are configured to be operated to impart motion to the housing and the attached medical device. The motion is configured to produce oscillatory motion of a frequency sufficient to concentrate shear stresses in a fluid boundary layer adjacent an inner wall of the medical device. The housing and the components supported in the housing are configured and arranged so that a device center of mass lies along or near the longitudinal axis of the channel.

21 Claims, 10 Drawing Sheets

Related U.S. Application Data

(60) Provisional application No. 61/835,065, filed on Jun. 14, 2013.

(51) Int. Cl.
  *A61M 25/02* (2006.01)
  *A61M 25/00* (2006.01)
  *A61B 90/70* (2016.01)

(52) U.S. Cl.
  CPC .............. *A61B 2090/701* (2016.02); *A61M 2025/0019* (2013.01); *A61M 2205/103* (2013.01); *A61M 2205/106* (2013.01); *A61M 2205/8206* (2013.01); *A61M 2206/16* (2013.01); *A61M 2209/10* (2013.01); *A61M 2210/101* (2013.01)

(58) Field of Classification Search
  CPC ........ A61M 2205/103; A61M 2209/10; A61M 2205/106; A61M 2025/0019; A61M 2206/16; A61M 2205/8206; A61B 2090/701
  See application file for complete search history.

(56) References Cited

U.S. PATENT DOCUMENTS

| | | | | |
|---|---|---|---|---|
| 3,850,580 | A | 11/1974 | Moore et al. | |
| 4,218,849 | A * | 8/1980 | Bodine | B24B 31/06 451/113 |
| 4,318,622 | A * | 3/1982 | Sterrenberg | B01F 11/0008 366/110 |
| 4,509,947 | A | 4/1985 | Lattin | |
| 4,555,183 | A | 11/1985 | Thomas | |
| 4,698,058 | A | 10/1987 | Greenfeld et al. | |
| 4,883,644 | A | 11/1989 | Perlman | |
| 4,906,238 | A | 3/1990 | Greenfeld et al. | |
| 4,932,935 | A | 6/1990 | Swartz | |
| 5,243,997 | A | 9/1993 | Uflacker et al. | |
| 5,380,273 | A | 1/1995 | Dubrul et al. | |
| 5,381,576 | A * | 1/1995 | Hwang | A61C 17/3481 15/22.1 |
| 5,399,013 | A | 3/1995 | Sawyer | |
| 5,443,078 | A | 8/1995 | Uflacker | |
| 5,449,369 | A | 9/1995 | Imran | |
| 5,524,635 | A | 6/1996 | Uflacker et al. | |
| 5,549,119 | A | 8/1996 | Solar | |
| 5,807,313 | A * | 9/1998 | Delk | A61M 1/0064 604/151 |
| 5,947,594 | A * | 9/1999 | Dolatli | B01F 11/0005 366/110 |
| 6,059,890 | A * | 5/2000 | Sedore | B08B 7/02 134/1 |
| 6,428,491 | B1 * | 8/2002 | Weiss | A61B 17/22012 601/2 |
| 6,457,482 | B1 * | 10/2002 | Cooper | B08B 3/12 134/117 |
| 6,852,097 | B1 | 2/2005 | Fulton, III | |
| 6,936,025 | B1 | 8/2005 | Evans et al. | |
| 7,892,191 | B2 | 2/2011 | Zumeris et al. | |
| 9,480,330 | B2 * | 11/2016 | Majeed | A46B 5/0095 |
| 2002/0055689 | A1 | 5/2002 | Kaplan et al. | |
| 2002/0193731 | A1 * | 12/2002 | Myers | A61M 1/062 604/74 |
| 2004/0199228 | A1 | 10/2004 | Wilson | |
| 2005/0038376 | A1 | 2/2005 | Zumeris et al. | |
| 2005/0058014 | A1 * | 3/2005 | Komori | B01F 15/00123 366/108 |
| 2006/0161098 | A1 | 7/2006 | Nita et al. | |
| 2006/0253154 | A1 | 11/2006 | Equils | |
| 2007/0009368 | A1 * | 1/2007 | Yang | A61M 1/0023 417/312 |
| 2007/0212265 | A1 | 9/2007 | Ebers et al. | |
| 2007/0244423 | A1 | 10/2007 | Zumeris et al. | |
| 2008/0097465 | A1 | 4/2008 | Rollins et al. | |
| 2008/0103419 | A1 | 5/2008 | Adamson | |
| 2008/0208083 | A1 | 8/2008 | Lin et al. | |
| 2009/0188531 | A1 | 7/2009 | Boyle, Jr. et al. | |
| 2009/0264833 | A1 | 10/2009 | Boyle, Jr. | |
| 2009/0281478 | A1 * | 11/2009 | Duke | A61B 17/34 604/22 |
| 2010/0180914 | A1 * | 7/2010 | Phillips | B08B 13/00 134/3 |
| 2010/0233021 | A1 | 9/2010 | Sliwa et al. | |
| 2010/0239352 | A1 * | 9/2010 | Huang | A45D 40/265 401/121 |
| 2013/0112620 | A1 * | 5/2013 | Mueller | A61M 1/1619 210/646 |
| 2013/0276248 | A1 * | 10/2013 | Majeed | B08B 9/00 15/21.1 |
| 2013/0338544 | A1 | 12/2013 | Newell | |
| 2014/0018766 | A1 * | 1/2014 | White | A61M 5/14 604/500 |
| 2015/0063056 | A1 * | 3/2015 | Kral | B01F 15/00746 366/110 |
| 2015/0313634 | A1 * | 11/2015 | Gross | A61B 1/3132 606/185 |
| 2017/0112589 | A1 * | 4/2017 | Ramkhelawan | A61B 1/127 |
| 2017/0265879 | A1 * | 9/2017 | Washburn, II | A61B 1/126 |
| 2018/0042643 | A1 * | 2/2018 | Norton | A61B 17/3423 |
| 2018/0214256 | A1 * | 8/2018 | Miyamichi | A61C 17/222 |
| 2020/0008611 | A1 * | 1/2020 | Sjaastad | A47J 31/06 |
| 2020/0054863 | A1 * | 2/2020 | Boyle, Jr. | A61M 27/00 |

* cited by examiner

MOTION-ASSISTED SYSTEMS, DEVICES AND METHODS FOR MINIMIZING OBSTRUCTION OF MEDICAL DEVICES

RELATED APPLICATION

This application is a continuation-in-part of U.S. patent application Ser. No. 14/301,770, filed on Jun. 11, 2014, which claims the benefit of U.S. Provisional Application No. 61/835,065, filed 14 Jun. 2013. The subject matter of these applications is incorporated herein by reference in their entireties.

GOVERNMENT FUNDING

This application was funded under National Heart, Lung and Blood Institute, National Institutes of Health (NIH), NIH Center for Accelerated Innovation at Cleveland Clinic (NCAI), (NIH-NHLBI 1UH54HL119810-01; NCAI-14-2-APP-CCF).

TECHNICAL FIELD

The present invention relates to systems, devices and methods for minimizing obstructions and maintaining patency in catheters and other medical devices having lumens or hollowed portions.

BACKGROUND

Catheters, such as chest tubes, are routinely used in patients who have had cardiothoracic surgery or chest trauma to drain blood and other biological matter. Use of chest tubes helps maintain cardiorespiratory/hemodynamic stability by avoiding complications related to accumulation of blood and thrombi (blood clots), air, debris, or other fluids in the pericardial sac and pleural space. However, chest tubes often clog after surgery and their occlusion can lead to life threatening complications such as hemothorax, acute tamponade, and pericardial effusion. This compromises postsurgical hemodynamics, adversely influences surgical outcome, and delays recovery. Chest drainage has recently been reported as an independent potential risk factor and predictor of mortality and is also associated with other adverse outcomes, including longer stays in the intensive care unit or hospital and increased duration on mechanical ventilation. Despite many improvements in intra-/post-operative care, chest-tube obstruction remains an important contributor to adverse effects on patients' adequate recovery after surgery. In serious cases, the surgeon brings the patient back into the operating room to remove clots around the heart to prevent pericardial tamponade and thus cardiogenic shock. This scenario suggests that the detriment in outcomes associated with postoperative bleeding may be related to inefficient clearing of blood and retained clots from the chest due to chest-tube clogging.

The management of chest tubes has traditionally consisted of makeshift mechanical methods such as milking and tapping the external portion of the tube to remove clots and maintain patency of the tubing. One of the more controversial methods is chest tube stripping, which can generate transient high negative intrathoracic pressure and can actually be detrimental to areas being drained. Milking of chest tubes may inadvertently push any clots back into the intrathoracic portion that may occlude the tube eyelets. It has also been shown that the degree of clogging cannot always be appreciated by inspecting the tubes prior to removal because the intrathoracic portion of the chest tube may be occluded even when the extrathoracic portion appears clear. This state of uncertainty emphasizes the critical need to address current chest tube clearance strategies or to find ways by which to test chest tube clearance systems as a way to improve outcomes and possibly reduce hospital costs. Barriers to progress in the field are how to prevent clogging and maintain patency for the full length of the tube, especially the intrathoracic portion where the side and end holes collect blood that has been shed within the chest.

Currently, there is no reliable method to prevent chest-tube clogging. A heparin coating allows small amounts of molecular heparin to diffuse into the tube's lumen and also makes the tube's inner surface slippery (low coefficient of friction), but this diffusion has a very limited time frame to maintain therapeutic efficacy. Another option is electroactive polymers embedded in the tube surface to alternately expand and contract, facilitating tube clearance. To reduce pain, drains that change from a larger diameter when placed within the body (to attain the largest drainage area possible) to a smaller diameter prior to removal have been proposed. Also, a variety of tubes with local anesthetics have been introduced to reduce the patient's discomfort and pain. Most solutions cannot provide a prolonged effect and/or cannot be controlled, safe and reliable at the same time. In addition, all existing solutions are limited in their mechanism of action to the tube's inner surface.

While there seems to be a general agreement on chest tube placement, there is little consensus on subsequent management. To date, there is no reliable method of preventing chest-tube clogging. The manual makeshift techniques in a combination with a negative suction remains the only actively reliable component to assist with the removal of blood, clots, and fluids from the chest. Solutions that involve internal coating to improve flow and prevent adhesion have limitations related to time and use duration. Ineffective drainage may take longer time to evacuate effusions. In its turn, longer period of drainage causes discomfort to patient, mechanical irritation to adjacent tissues, increased risk of infection and require an additional tube placement.

Therefore new and more efficient systems, devices and methods to prevent clot formation on both inner and outer surfaces of chest tubes, catheters, and other medical devices with lumens and to maintain patency of drainage tubes is necessary to reduce clot accumulation within the chest and complications linked to that condition. Further, there is a need for a chest-tube drainage system and method that reliably can be implemented without concern for clogging, not only for heart and lung surgery, but especially for expanding minimally invasive and higher acuity urgent and emergent cases.

SUMMARY

In general, the present invention provides systems, devices and methods to minimize occlusion of catheter's lumen by a substance, help maintain the catheter's patency, improve and/or enhance the functionality of the catheter, remotely or directly provide short-term or long-term effects on biological substances inside the catheter and or in the area surrounding the catheter.

In particular, the present invention provides a catheter drainage system, such as a chest tube drainage system, that applies mechanical motion to the lumen of the catheter to minimize blood clots and/or other biological substances from adhering to the catheter walls when the walls are moving. The mechanical motion applied to the catheter preferably prevent biological substances from adhering to inner walls and preferably also outer walls of the catheter to prevent clogging inside (and preferably also outside) the catheter and to maintain the patency of the catheter.

In an embodiment, the present invention provides a device comprising a body configured to attach to a catheter in an operative state. The catheter has a proximal end, a distal end, and a lumen therebetween. The body comprises a housing including a mechanical motion source electrically coupled to an electrical energy source in an operative state. The mechanical motion source is configured to deliver mechanical motion to the catheter along the lumen, preferably towards the distal end. The mechanical motion is sufficient to minimize obstruction of the catheter by a biological substance. Preferably, the mechanical motion prevents, minimizes or otherwise influences adherence of a biological substance to the inner and/or outer wall of the catheter. The mechanical motion also preferably prevents or affects solidification of biological fluids and their derivates at intended level. Also, preferably the mechanical motion helps maintain the catheter's patency inside and/or outside the patient's body. Further, preferably the mechanical motion helps maintain the catheter's flow characteristics.

In another embodiment, the present invention provides a system comprising a catheter and a device. The catheter has a proximal end, a distal end, and a lumen therebetween. The device comprises a body configured to couple to the catheter in an operative state. The body comprises a housing including a mechanical motion source electrically coupled to an electrical energy source in an operative state. The mechanical motion is configured to deliver mechanical motion to the catheter along the lumen, preferably towards the distal end. The mechanical motion is sufficient to minimize obstruction of the catheter by a biological substance. Preferably, the mechanical motion prevents, minimizes or otherwise influences adherence of a biological substance to the inner and/or outer wall of the catheter. The mechanical motion also preferably prevents or minimizes solidification of biological fluids and their derivates. Also, preferably the mechanical motion helps maintain the catheter's patency inside and/or outside the patient's body. Further, preferably the mechanical motion helps maintain the catheter's flow characteristics.

In another embodiment, the present invention provides a method of minimizing obstruction of a catheter having an interior portion configured to be disposed inside a patient's body, an exterior portion configured to be disposed outside of a patient's body, a proximal end, a distal end, and a lumen between the proximal and distal ends. The method comprises delivering mechanical motion to the catheter along the lumen, preferably towards the distal end. The mechanical motion is sufficient to minimize obstruction of the catheter by a biological substance. Preferably, the mechanical motion prevents, minimizes or otherwise influences adherence of a biological substance to the inner and/or outer wall of the catheter. The mechanical motion also preferably prevents or minimizes solidification of biological fluids and their derivates. Also, preferably the mechanical motion helps maintain the catheter's patency inside and/or outside the patient's body. Further, preferably the mechanical motion helps maintain the catheter's flow characteristics.

According to one aspect, a device for minimizing obstruction in a medical device that carries fluids includes a housing defining a channel configured to receive and secure a section of the medical device such that the section of the medical device extends coaxially with a central longitudinal axis of the channel. Components, including a motor, are supported in the housing and are configured to be operated to impart motion to the housing and the attached medical device. The motion is configured to produce oscillatory motion of a frequency sufficient to concentrate shear stresses in a fluid boundary layer adjacent an inner wall of the medical device. The housing and the components supported in the housing are configured and arranged so that a device center of mass lies along or near the longitudinal axis of the channel.

According to another aspect, alone or in combination with any other aspect, the components can also include one or more batteries. The batteries and the motor can be spaced about the longitudinal axis both radially and circumferentially to place the device center of mass along or near the longitudinal axis of the channel.

According to another aspect, alone or in combination with any other aspect, the motor can include a DC motor and the components can include an eccentric weight connected the motor, one or more batteries, and a controller for controlling electrical current directed to the motor from the one or more batteries in order to control the operation of the motor.

According to another aspect, alone or in combination with any other aspect, the housing can have a lobed configuration including a plurality of lobes spaced generally equally about the longitudinal axis both radially and circumferentially.

According to another aspect, alone or in combination with any other aspect, one of the lobes can house the motor and the remaining lobes can house the one or more batteries.

According to another aspect, alone or in combination with any other aspect, the components can be configured such that the mass of the components housed in each lobe is about the same.

According to another aspect, alone or in combination with any other aspect, the components housed in the lobe that houses the motor can include an eccentric weight connected to the motor and a controller for controlling electrical current directed to the motor from the one or more batteries in order to control the operation of the motor.

According to another aspect, alone or in combination with any other aspect, the lobes can be configured to receive the components. Each lobe can be configured to have a mass that, when combined with the mass of the components housed in the lobe, is about equal to each of the other lobes.

According to another aspect, alone or in combination with any other aspect, the medical device can be a tube for carrying body fluids, and/or the medical device can be a catheter for carrying body fluids, and/or the medical device can be a chest tube for carrying body fluids.

According to another aspect, alone or in combination with any other aspect, the frequency can be in the range of 50-200 Hz.

According to another aspect, alone or in combination with any other aspect, the oscillatory motion can induce swirl in the fluids in the medical device.

According to another aspect, a device for minimizing obstruction in a medical device that carries fluids can include a housing defining a channel configured to receive and secure a section of the medical device such that the section of the medical device extends coaxially with a central longitudinal axis of the channel. The device can also include components supported in the housing, including a motor operable to impart motion to the housing and one or more batteries for supplying electrical energy for operating the motor. The motion is configured to impart motion to the housing and the attached medical device and to produce oscillatory motion of a frequency sufficient to concentrate shear stresses in a fluid boundary layer adjacent an inner wall of the medical device. The motor and each of the one or more batteries are spaced from each other generally equally about the longitudinal axis both radially and circumferentially.

According to another aspect, alone or in combination with any other aspect, the frequency can be in the range of 50-200 Hz.

According to another aspect, alone or in combination with any other aspect, the oscillatory motion can induce swirl in the fluids in the medical device.

According to another aspect, alone or in combination with any other aspect, the housing can have a lobed configuration comprising a lobe for receiving the motor and components associated with the motor and a lobe for receiving each of the one or more batteries and the components associated with the one or more batteries. The lobes can be spaced from each other generally equally about the longitudinal axis both radially and circumferentially.

According to another aspect, a device for minimizing obstruction in a medical device includes a housing defining a channel configured to receive and secure a section of the medical device such that the section of the medical device extends coaxially with a central longitudinal axis of the channel. The device also includes a motor operable to impart motion to the housing and one or more batteries for supplying electrical energy for operating the motor. The housing has a lobed configuration comprising a lobe for receiving the motor and components associated with the motor, and a lobe for receiving each of the one or more batteries and the components associated with the one or more batteries. The lobes are spaced from each other generally equally about the longitudinal axis both radially and circumferentially.

According to another aspect, alone or in combination with any other aspect, the motion imparted to the housing can impart motion to the attached medical device. The motion can be configured to produce oscillatory motion of a frequency sufficient to concentrate shear stresses in a fluid boundary layer adjacent an inner wall of the medical device.

According to another aspect, alone or in combination with any other aspect, the motion imparted by the motor can be at a frequency in the range of 50-200 Hz.

According to another aspect, alone or in combination with any other aspect, the oscillatory motion can induce swirl in the fluids in the medical device.

DETAILED DESCRIPTION

Figure 1:
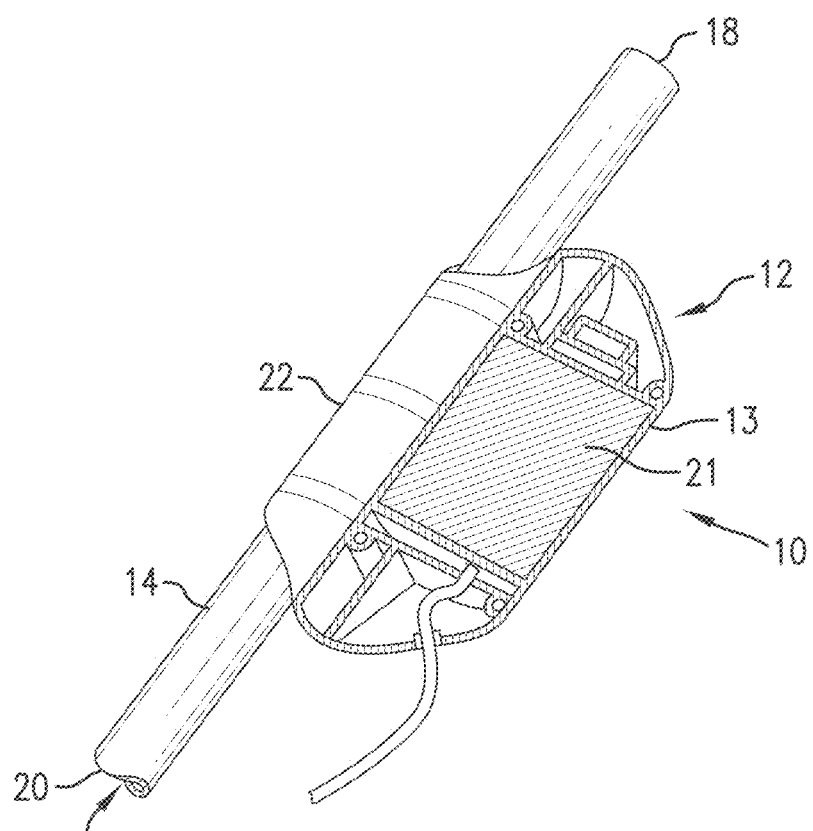
FIG. 1 is a cross-sectional view of an embodiment of a device of the present invention attached to a medical device.

Although embodiments of the present invention will be described with respect to a chest tube drain or catheter, the systems, devices and methods can apply to other types of medical device having a lumen or hollowed area that is at risk of becoming occluded and/or collapsing. Non-limiting examples of such medical devices include drainage tubes, catheters (tubular and non-tubular), fluid lines, other tubular structure, and devices with hollow bodies. Further, although embodiments of the present invention will be described with respect to a blood clot occluding a catheter, the present invention provides systems, devices and methods to minimize or prevent catheter obstruction by other fluids, including other biological fluids. In addition, although the mechanical motion delivered to the medical device will be described with respect to delivering a vibratory force, other types of mechanical motion can be applied to the medical device such as fluctuation or oscillation. Further, although a motor is mostly described as the mechanical motion source, other motion sources can be used such as an electric motor, a mechanical and/or electro-mechanical system that powers the device and/or assists, accelerates, or enhances the device with motion or any other suitable energy activated device or system. Also, electrical motion can also be applied to the medical device so long as the motion achieves the purposes as disclosed herein.

The disclosure herein refers to a patient. A patient is a mammal, including a human being. The disclosure herein also refers to an "operative state." This is the configuration of the system or device when the device is applying or is ready to apply motion to the catheter. By "integral" or "integrated" is meant that the described components are molded as one piece during manufacturing or the described components are otherwise not separable using a normal amount of force without damaging the integrity (i.e. tearing) of either component. A normal amount of force is the amount of force a user would use to remove a component meant to be separated from the other component without damaging either structure. Further, as used herein with respect to a described component, the terms "a," "an," and "the" include at least one or more of the described component, feature or element unless otherwise indicated. Moreover, the term "or" includes the term "and/or" unless otherwise indicated. In addition, it will be understood that when an element is referred to as being "on," "attached" to, "connected" to, "coupled" with, "contacting," etc., another element, it can be directly on, attached to, connected to, coupled with, or contacting the other element or intervening elements may also be present. In contrast, when an element is referred to as being, for example, "directly on," "directly attached" to, "directly connected" to, "directly coupled" with, or "directly contacting" another element, there are no intervening elements present.

In an embodiment, the present invention provides a catheter drainage system, such as a chest tube drainage system, that apply vibration to the lumen of the catheter to minimize blood clots and/or other biological substances from adhering to the catheter walls when the walls are vibrating. In a preferred embodiment, the vibration or vibratory force is applied to the entire length of the catheter's lumen. If clots cannot stick to the chest tube wall, the risk of clot buildup and tube occlusion is greatly reduced. Methods of the present invention maintain chest tube patency, which eliminates potential complications and liberates caregivers from performing repetitive inspections and manipulations at the bedside. Also, since drainage is assisted, there is no or minimal clot obstruction. As such, chest tube size may be reduced to lessen pain, improve wound healing, and provide better patient comfort postoperatively. Generally, small chest tubes are considered to be more likely to clog. However, smaller chest tubes can be as effective as large tubes in draining fluid if enhanced by vibrational motion to prevent blood clotting inside the tubes according to methods of the present invention.

Accordingly, embodiments of the present invention can reduce the complications and pain associated with obstructed chest tubes thus improving outcomes and survival. One way in which pain can be reduced is by using smaller diameter tubes. Embodiments of the present invention prevent or minimize intra-tube depositions and maintain tube patency. In addition, systems can increase short and long term performance of biomedical catheters and devices that are exposed to the blood stream (such as, for example, chest tubes, scopes, lines, other biomedical tubes, and needles), when changes in intraluminal fluid characteristics may create an obstruction.

With reference to FIG. 1, in an example configuration, device 10 comprises body 12. Body 12 comprises a housing 13 configured to couple to catheter 14 in an operative state. Only a portion of catheter 14 is illustrated in FIG. 1. Catheter 14 comprises a proximal end towards section 16, a distal end towards section 18 and a lumen 20 extending therebetween. Housing 13 comprises a mechanical motion source, such as a vibration source, electrically coupled to an electrical energy source (not shown) in an operative state. FIG. 1 illustrates the vibration source being a motor 21. The motor is configured to deliver mechanical motion, such as a vibratory force, to the catheter along lumen 20, preferably towards distal end of section 18. The mechanical motion is sufficient to minimize obstruction of catheter 14 by a biological substance, such as a blood clot. In preferred embodiments, the mechanical motion is sufficient to apply motion to the entire length of the catheter. This may prevent the initial deposit of blood and therefore subsequent clot formation. Thus, since there is no clot buildup, no obstruction can occur and the tube remains patent. Also preferably, the mechanical motion delivered by the motor is sufficient to prevent clot attachment to not only the catheter's inner surface but also the catheter's outer surface, which can improve drainage through open apertures of the catheter. The mechanical motion can also affect the contacting surface of the catheter with the tissues as the insertion site. This mechanical motion, such as a vibratory force, and its unique "swirling" effect on fluid inside the tube can enhance the functional characteristics of current catheters, such as chest tubes. On the outside of the tube, the vibration can improve circulation in the tissues surrounding the catheter.

Regarding the power source, preferably the power source allows the user to select customized amplitudes, frequencies and/or current of the electrical energy delivered to the device. Regarding the vibration source, preferably the vibration source, such as a motor, can change the levels of vibration conveyed to the catheter thus enabling adjustability of amplitude to each given clinical condition. Further systems can include a motor with ball bearings that can be sealed and a controller. Further, the motor can have various speeds, which will increase the vibrational frequency range, allowing the most efficacious amplitude and frequency to be utilized. To this end, the motor can also include a speed controller to maintain set constant frequencies. In another embodiment, a device includes a motor with the eccentric mass as an assembled unit. Preferably, there is a sealed interface around the motor and vibrating mass.

Figure 2:
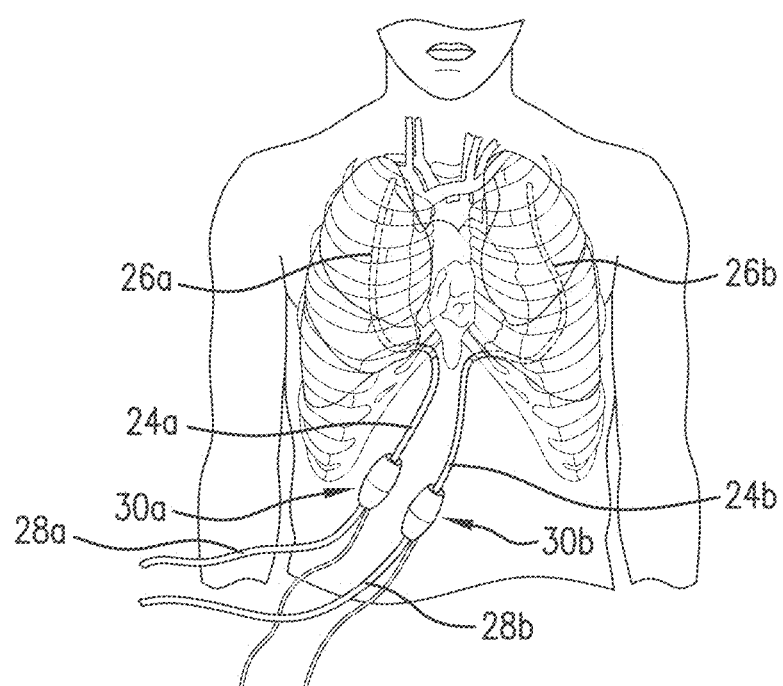
FIG. 2 is a schematic illustration of a patient's upper body with an embodiment of devices of the present invention coupled extrathoracically to chest tubes.

In the embodiment shown in FIG. 1, body 12 further comprises a fixation mechanism, such as clamp 22 connected to housing 13. Clamp can be integral with housing 13. Clamp 22 is configured to removably attach to catheter 14 in an operative state. A clamp is only one example of a suitable fixation member. Other fixation members can be used such as a clip, suction, clasp, sleeve, male-female fasteners, or any suitable combination thereof. In certain embodiments, the body of a device is integrally attached to the catheter providing an integrated system comprising a device and catheter as described in more detail below. FIG. 2 is a schematic illustration of an embodiment of a device 30 of the present invention and accompanying components inserted in a patient's body. Catheter 24 has an interior portion 26 inside the patient's body and an exterior portion 28 outside of the patient's body. In a preferred embodiment and as depicted in FIG. 2, device 30 is attached to the exterior portion 28 of the catheter 24.

Figure 3:
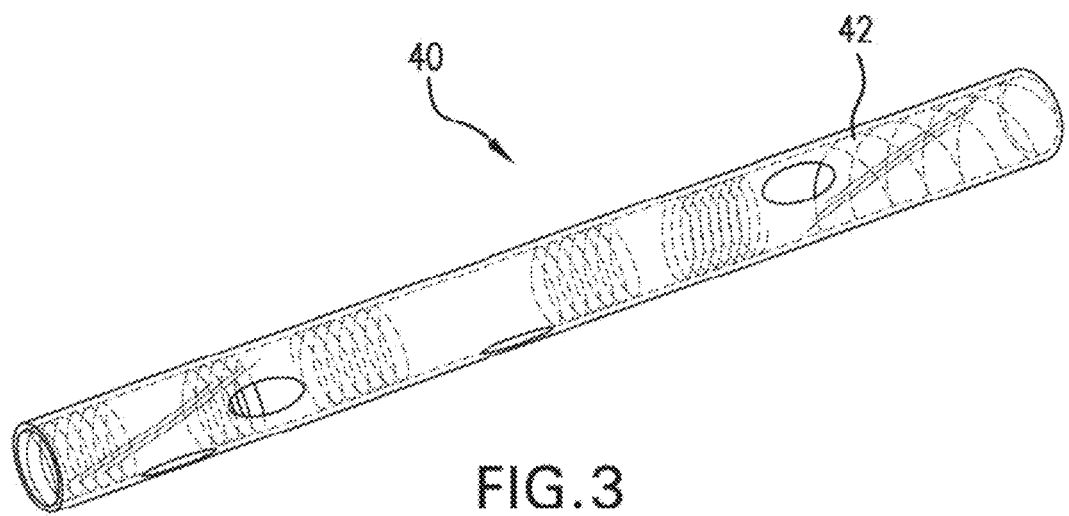
FIG. 3 is a perspective view of an embodiment of an integrated catheter, in particular a chest tube tip, according to the present invention. The walls of the catheter are enhanced with metallic components (several rods wrapped within the chest tube wall).
Figure 4:
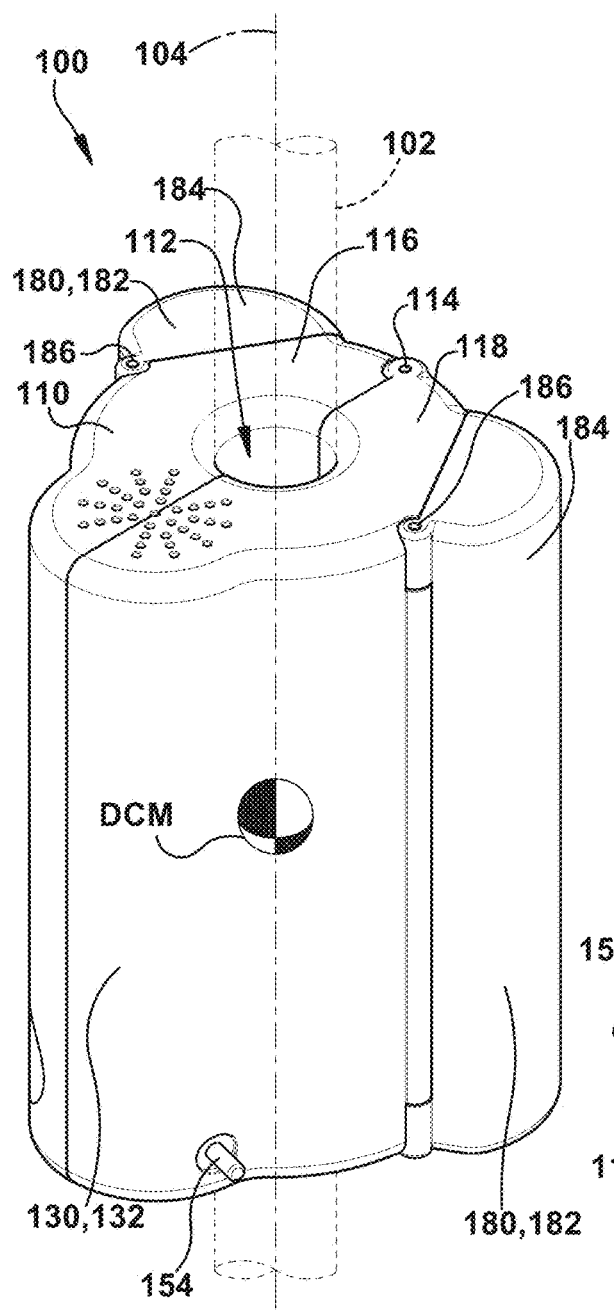
FIGS. 4 and 5 are perspective views illustrating another example configuration of a device in a closed condition, according to the invention.
Figure 5:
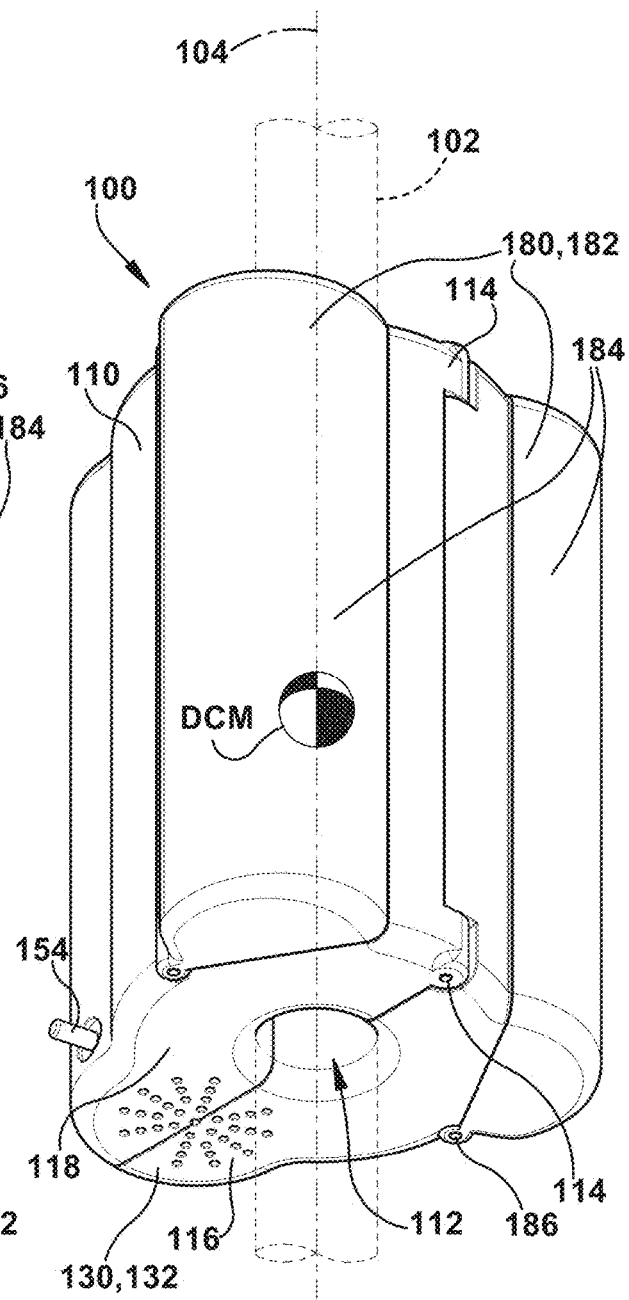

In embodiments, the present invention provides an integrated system comprising a device integrally connected to a catheter, such as a chest tube. The catheter can have the diameter of a standard chest tube (32-40 Fr), or a smaller or larger diameter than standard chest tubes. In certain embodiments, the catheter has a diameter of about 20 Fr. The inner and outer surface of the catheter can be fabricated from a soft polymer, such as polyvinyl chloride. The walls of the tube can be enhanced with metallic components. Referring to FIG. 3, in an embodiment, several rods 42 are helically wrapped or braided within the chest-tube or catheter 40 wall. The number of rods and the helical pitch can be chosen to balance the goal of improved vibration transmission while avoiding stiffening the tube to the point where it is difficult to insert and possibly uncomfortable for the future patient. In another embodiment, the catheter is a custom laser-cut metal tube that allows flexing but still sufficient axial stiffness and capacity for improved vibration transmission. Since the laser-cut tube is a monolithic component, it will facilitate fabrication and may provide better vibration transmission. The catheter can include additional metallic components embedded in the chest-tube wall at the distal end to attenuate the vibration at this location. The vibration source can be directly coupled to the metallic elements within the integrated chest tube. Such vibration sources include piezoelectric actuators and solenoid mechanisms. In certain embodiments, the present invention provides a kit with an integrated system that includes different sizes of catheters, such as different chest tube sizes.

The system can also include an integrated power source. Preferably, the integrated system including the device and catheter is a single disposable unit. By "disposable" is meant that the device is not intended to be used more than a select number of times, such as one time.

In any of the embodiments of systems and devices of the present invention, preferably the devices are water-resistant. Also, to minimize patient discomfort due to potential pain from vibration, the devices of the present invention can be covered with an extrathoracic device cover in which the device is internally suspended. Further preferably, embodiments of systems of the present invention are instrumented to obtain one or more of the following measurements: 1) motor speed or frequency; 2) motor current; 3) vibration amplitude at the interface of the clamp and the chest tube or some other useful position on the device; 4) vibration amplitude at the distal end of the chest tube; and 5) vibration frequency at the distal end of the chest tube.

The present invention also provides embodiments of methods of minimizing obstruction of a catheter, such as a chest tube. In an embodiment, a method of minimizing obstruction of a catheter comprises delivering vibratory force to the catheter along the lumen towards the distal end of the catheter. The vibratory force is sufficient to minimize obstruction of the catheter by a biological substance. The vibratory force can be applied to the catheter by a motor or other vibration source that delivers vibration to the catheter sufficient to minimize catheter obstruction. Preferably, the vibratory force prevents or minimizes adherence of a biological substance to the inner and/or outer wall of the catheter and also help maintain the catheter's patency.

In an exemplary method, chest tubes are inserted in a patient's chest. The device body is tightly coupled (no tube compression) with the chest tubes inserted into the chest, exteriorized through the anatomical layers and secured to skin in a standard fashion as shown in FIG. 2. To complete the setting, the distal end of the chest tube is connected to collection canister with a vacuum suction attached (approximately 10-20 mm Hg). When the device is turned ON, the motion is conveyed to the functional portion (segment with holes and openings) of the chest tube (towards the internal portion of the tube and the tip). In particular, the electrical energy source is turned on to activate the motor and the vibration effect is conveyed along the tube inside the body towards the distal end of the tube.

The device can be an external attachment unit that does not interact directly with the sterile environment inside the tube and does not compromise the standard clinical setting of chest-tube use. In addition, the device can prevent or minimize clot attachment from the tube's outer surface as well, which in turn improves drainage through the holes of the tube that are kept open. This vibrational motion and its unique swirling effect on fluid inside the cylindrical tube is enhances the functional characteristics of the chest tubes currently used in cardiothoracic practice. However, as stated above, the device can be used in other settings where catheter occlusion is a risk factor.

Another example configuration of the device is illustrated in FIGS. 4-9. In this example configuration, a motion-assist ("MAS") device 100 for applying motion to a tube 102 in the form of a catheter, such as a chest tube for draining blood and other fluids from a patient's chest cavity after a surgical procedure, such as open-heart surgery. The MAS device 100 includes a housing 110 including an open central channel 112 for receiving the tube 102. The channel 112 is cylindrical and extends along a central axis 104 of the MAS device 100. As shown in the figures, the channel 112 is centered or substantially centered within the general cross-sectional shape of the housing 110. The central axis 104 therefore serves as the longitudinal axis for the MAS device 100, the housing 110, and the channel 112, and can also be considered an axis of symmetry.

The MAS device 100 includes first and second housing halves 116, 118 that are connected for pivotal movement relative to each other by a hinge 114. Each housing half 116, 118 includes a semi-cylindrical portion, i.e., half of the central channel 112. The housing 110 can thus be placed in an open condition (see, e.g., FIG. 6) for receiving the tube 102 in the channel 112 and can thereafter be closed around the tube, latching together the housing halves 116, 118 to connect the MAS device 100 to the tube. To this end, the dimensions of the housing halves 116, 118, specifically their respective semi-cylindrical portions, can be selected to receive and clamp onto a preferred tube size or size range, depending on the application. For instance, the dimensions of the housing halves 116, 118 can be selected so that the central channel 112 is configured to receive and clamp onto a standard 32 French polyvinyl chloride (PVC) chest tube catheter.

The latching of the housing 110 can be facilitated in a variety of manners. For example, the housing 110 can be latched via magnetic latching elements 120, such as permanent (e.g., rare earth) magnets. Alternatively, latching together the housing halves 116, 118 could be facilitated by a mechanical latch or by fasteners, such as screws.

To facilitate a secure connection of the MAS device 100 onto the tube 102, the surfaces forming the channel 112 can be configured to apply an appropriate grasping force onto the tube 102. This can be achieved, for example, via a slight interference between the inside diameter of the channel 112 and the outside diameter of the tube 102. This can also be achieved by coating or otherwise forming the inner surface of the channel 102 using a material or coating (e.g., adhesive) to form the surface of the channel 112 that facilitates opening the housing 110. This can also be achieved through the use of surface features, such as knurling or ribs, which are illustrated by way of example at 122 and 124, respectively in FIG. 6).

Figure 8:
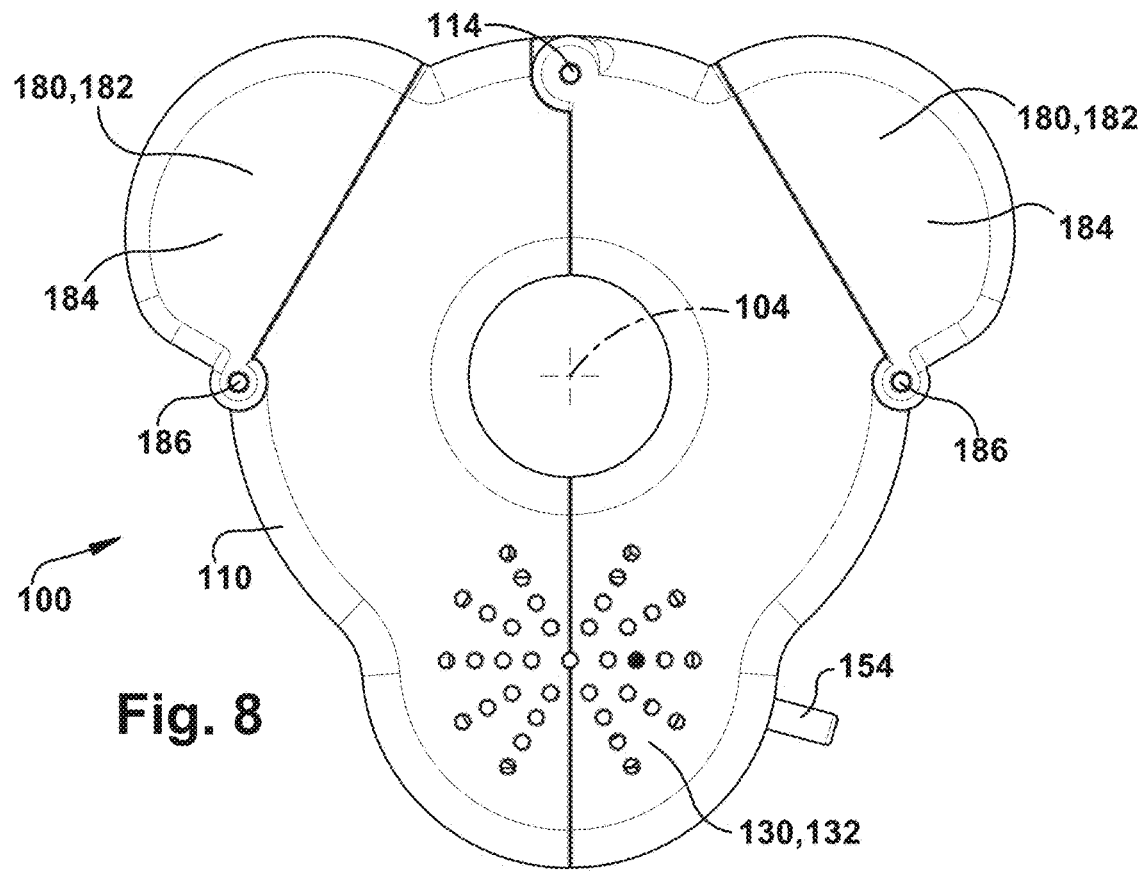
FIG. 8 is a top view illustrating the device of FIGS. 4 and 5.
Figure 9:
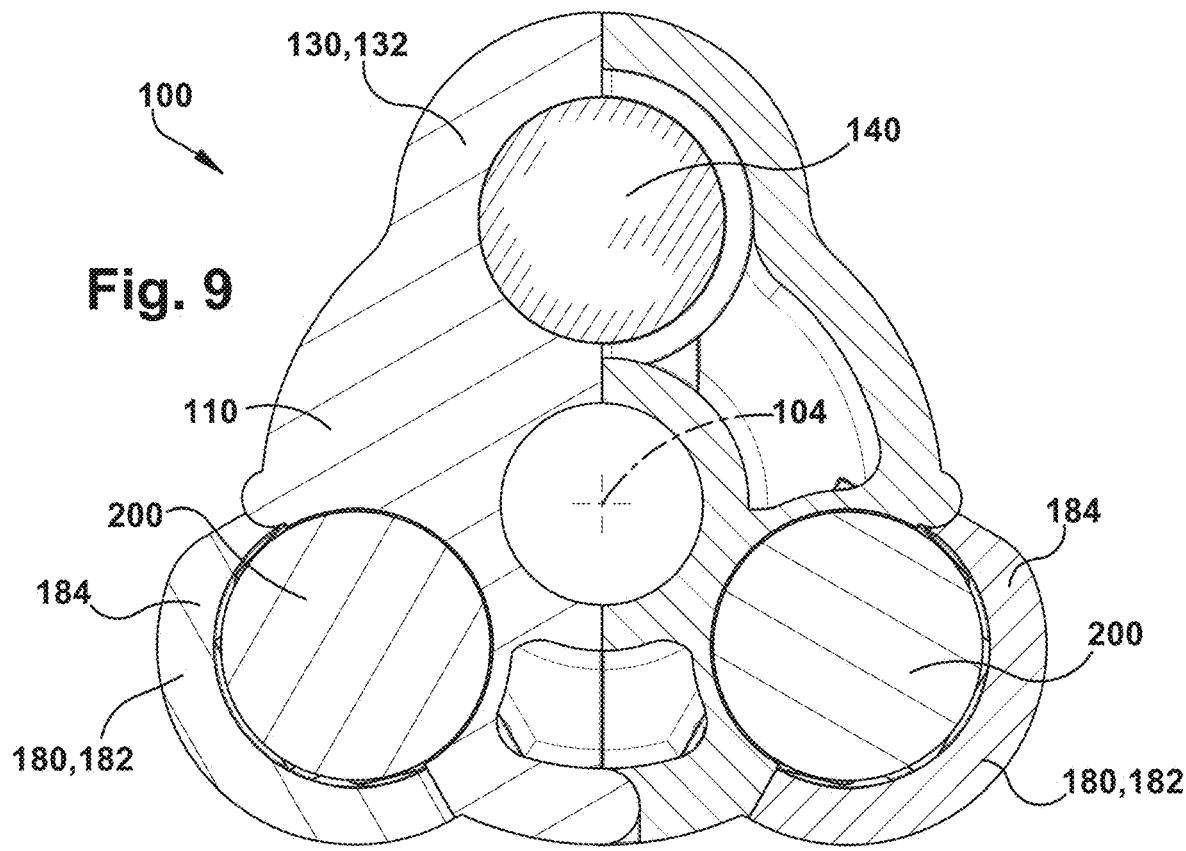
FIG. 9 is a sectional view illustrating the device of FIGS. 4 and 5.

In the example configuration, the MAS device 100 has a generally tri-lobular design in which three semi-cylindrical lobes are spaced 120 degrees from each other. This is best shown in FIGS. 8 and 9. These lobes include a motor lobe 130 and two battery lobes 180. Similarly, the housing 110 includes three compartments, each of which is corresponds to one of the three lobes of the MAS device 100. A motor compartment 132 forms the portion of the housing 100 that forms the motor lobe 130. Two battery compartments 182 form the portions of the housing 110 that form the battery lobes 180.

Figure 6:
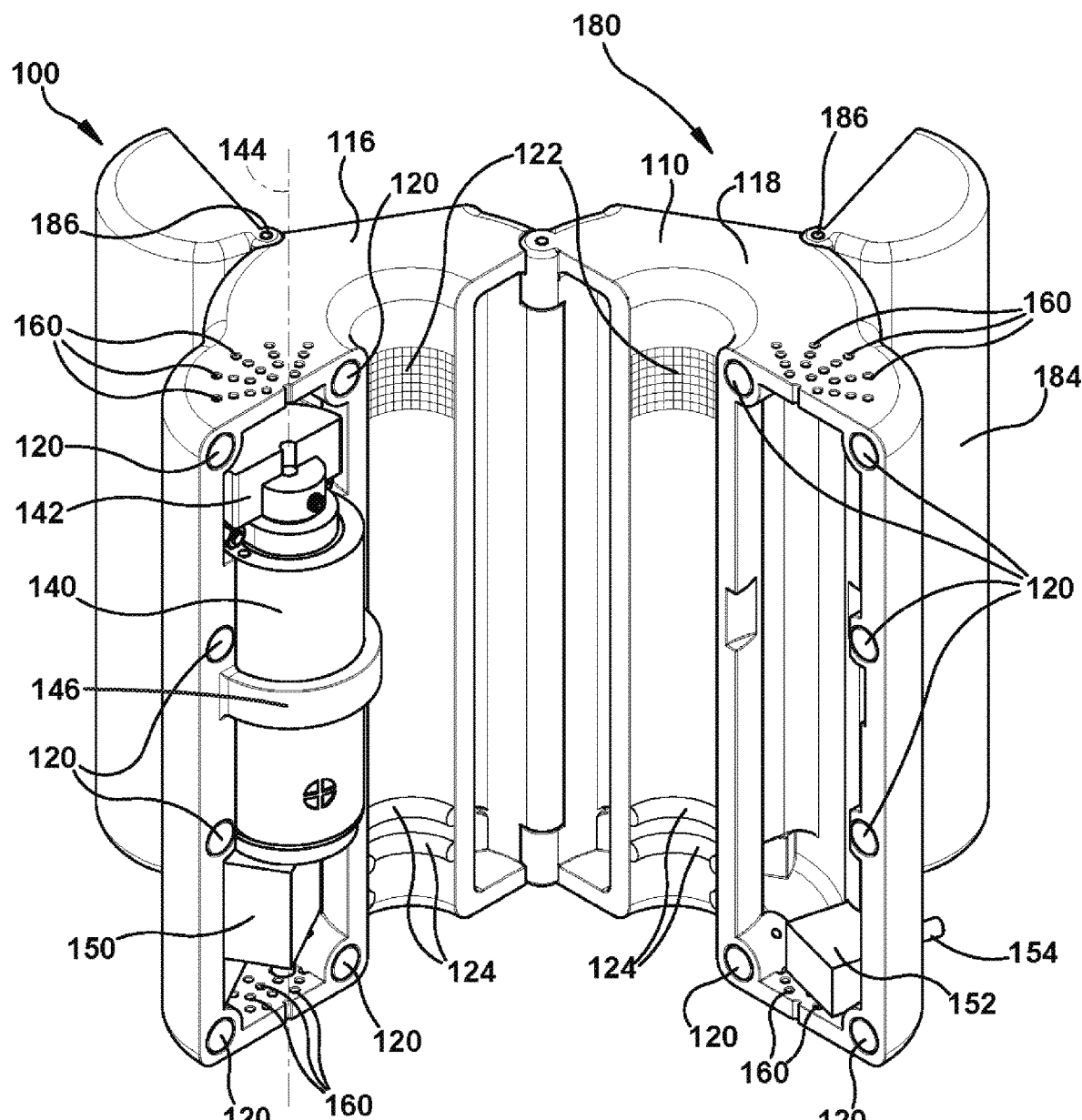
FIG. 6 is a perspective view illustrating the device of FIGS. 4 and 5 in an open condition.
Figure 7:
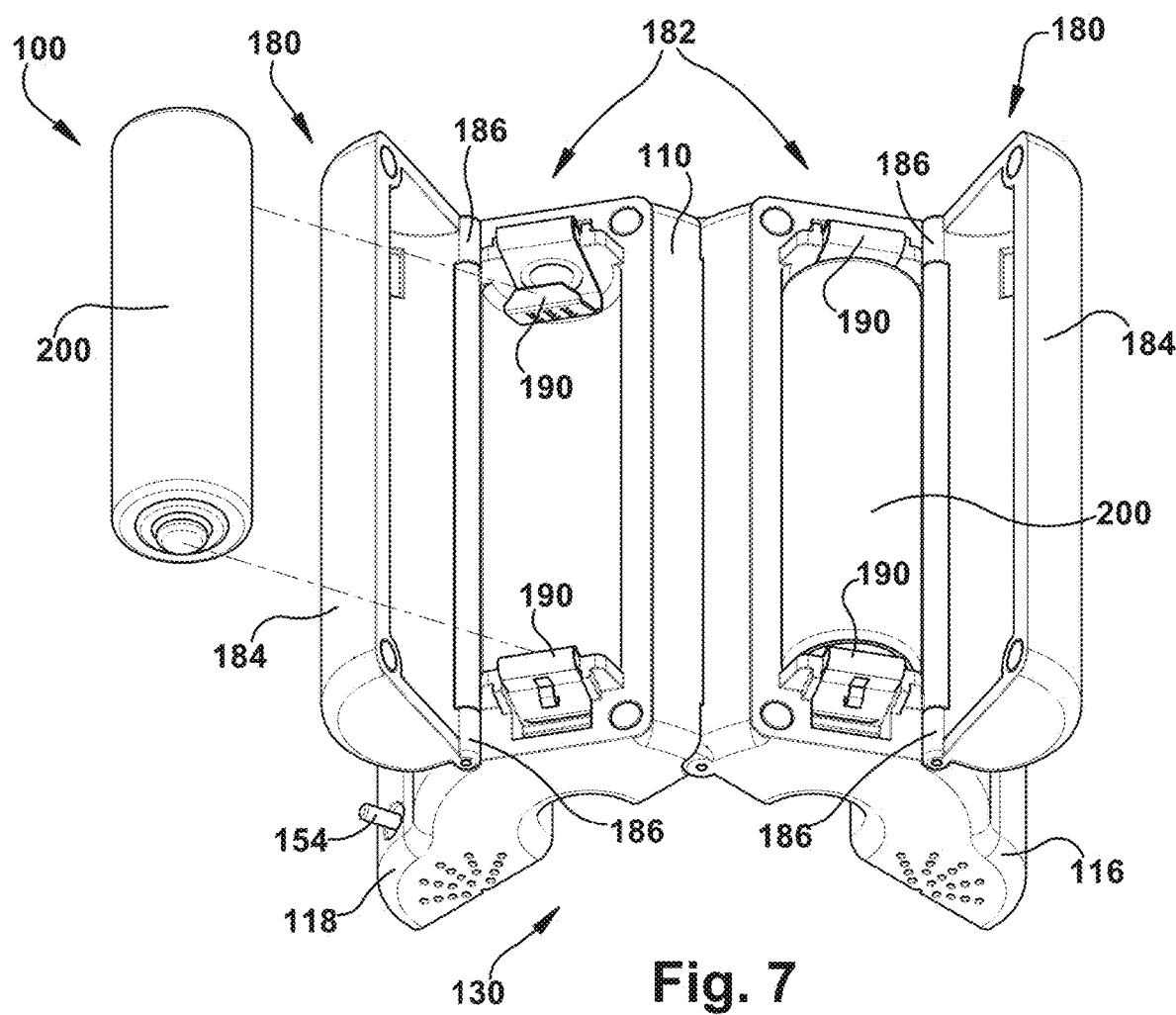
FIG. 7 is a perspective view, partially exploded, illustrating the device of FIGS. 8 and 9 in an open condition.

The motor compartment 132 opens and closes with the opening and closing of the housing 110 facilitated by the hinge 114. Referring to FIG. 6, the motor compartment 132 houses a motor 140, such as a high-precision DC motor, that supports an eccentric weight 142 for rotation about a motor axis 144. The motor compartment 132 also houses a motor controller 150 for controlling the operation of the motor 140. The motor controller 150 can perform a variety of functions, such as motor speed control and motor speed cycling control, and can include indicators, such as LEDs for indicating the operating status of the MAS device 100. The motor compartment 132 further houses a motor switch 152 for controlling the power supplied to the motor 140 and controller 150. The switch 152 can include a toggle 154 that extends through the housing wall to facilitate switching the MAS device 100 on and off during use. Additionally, the motor compartment 132 can include vent holes 160 for providing ventilation and cooling for the motor 140.

Each battery compartment 182 includes a door 184 that is secured by a hinge 186 that facilitates opening and closing its associated compartment. The doors 184, when closed, can be latched closed in a variety of manners. For example, the doors 184 can be latched via magnetic latching elements 186, such as permanent (e.g., rare earth) magnets. Alternatively, latching closed the doors 184 could be facilitated by a mechanical latch or by fasteners, such as screws.

Each battery compartment 182 is configured to receive and support a battery 200. Each battery compartment 182 also houses a pair of battery contacts 190 configured to receive and mate with corresponding terminals of their respective batteries 200. The battery contacts 190 can be spring biased so as to exert a resilient spring force on the battery terminals in order to maintain good electrical contact and to secure each battery 200 in its associated compartment 182.

In operation, the MAS device 100 imparts a circular, oscillating motion to the tube 102 through the motor's rotating the eccentric weight 142 about the motor axis 144. The system, i.e., the MAS device 100 and tube 102 with fluid inside, can be viewed as a cylindrical column of fluid surrounded by a gyrating tube. The circular oscillating motion of the tube 102 results in both rotational and axial oscillating movement of the tube relative to the fluid column in the tube. This relative movement between the tube 102 and the fluid causes shear stresses concentrated in a thin boundary layer of fluid along the inner surface of the tube. It is these shear stresses in the thin boundary layer of fluid that prevent the accumulation of fluids due to clotting, coagulation, thrombus, etc. on the inner wall of the tube 102.

The fluid column within the tube 102 exhibits inertia that resists movement with the oscillating tube, and it is this inertia that makes possible the movement of the tube relative to the fluid and the resulting desirable effects of concentrating shear stresses in the thin boundary layer next to the inner wall of the tube. The frequency and amplitude of the oscillatory motion imparted to the tube 102 by the MAS device 100 affects how the fluid in the tube responds. The oscillating frequency of the imparted tube motion is determined, of course, by the motor speed rotating the eccentric mass. The amplitude of the imparted tube motion is determined both by the mass of the eccentric mass and the radius or offset of its center of mass size from the axis of rotation.

Assuming an appropriate amplitude of the oscillating motion, if the oscillating frequency of the tube 102 is too low, the tube and the fluid will move together in unison, shear stresses will not be produced in the boundary layer, and the formation of clotting, coagulation, thrombus, etc. can result. If the oscillating frequency of the tube 102 is high enough, the inertia of the fluid column will not be overcome and the result is the desired relative tube movement and the resulting shear stresses that help prevent clotting, coagulation, thrombus, etc. build-up. If, however, the oscillating frequency of the tube 102 is too high, the system will produce unnecessary noise and power consumption, and the potential for bearing wear.

Similarly, assuming an appropriate oscillating frequency, if the amplitude of the oscillating motion is too low, the magnitude of any resulting shear stresses can be insufficient to prevent clotting, coagulation, thrombus, etc. If the amplitude of the oscillating motion sufficiently high, the inertia of the fluid column will not be overcome and the desired relative tube movement and resulting shear stresses will ensue. If, however, the oscillating frequency of the tube 102 is too high, the system will produce unnecessary noise and power consumption, and the potential for bearing wear.

Testing confirmed the effectiveness of the MAS device 100. Clinical testing on post-operative human subjects proved that the MAS device 100 can be used on a chest tube without causing any significant discomfort to the patient. In vivo animal testing proved that the MAS device was effective in preventing clotting, coagulation, thrombus, etc. on the inner and outer walls of a chest tube along a significant length of the tube, both at the location of the MAS device 100 and remotely therefrom.

Figure 10A:
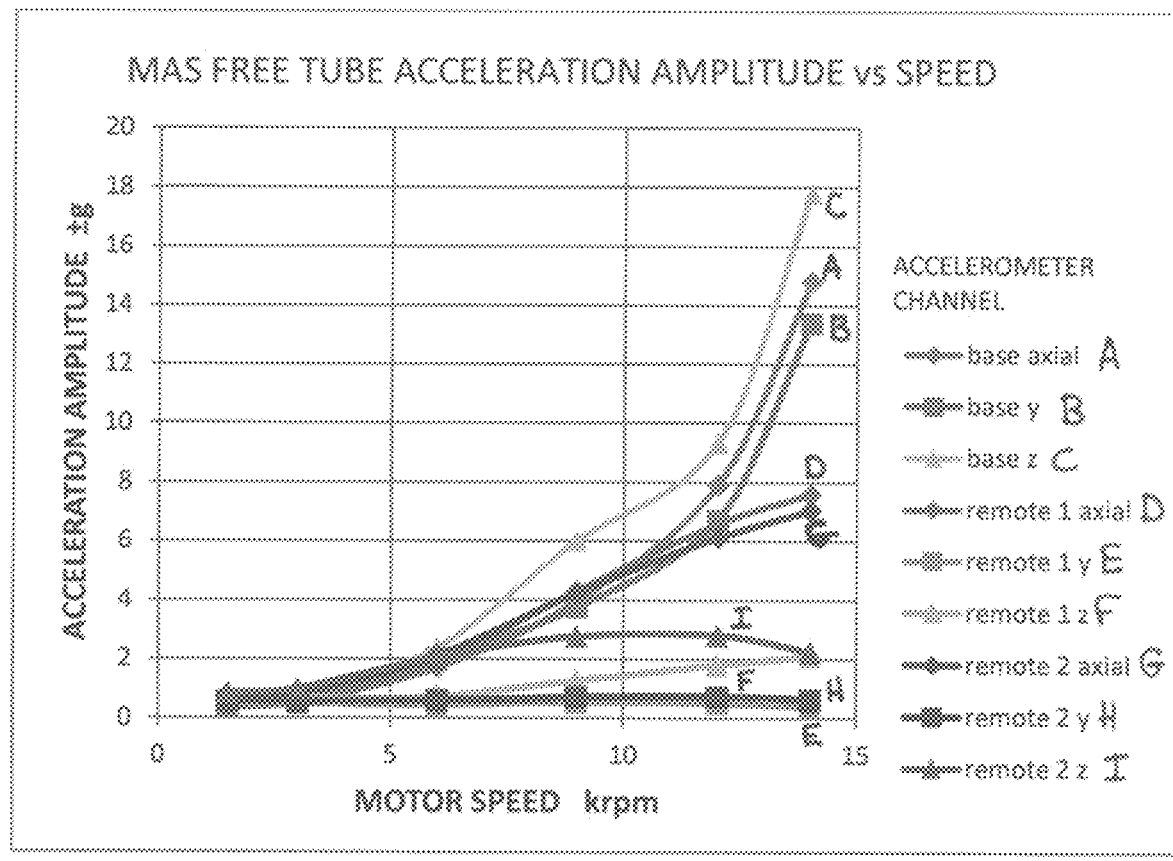
FIGS. 10A-10C are graphs illustrating the efficacy of the device under testing conditions.
Figure 10B:
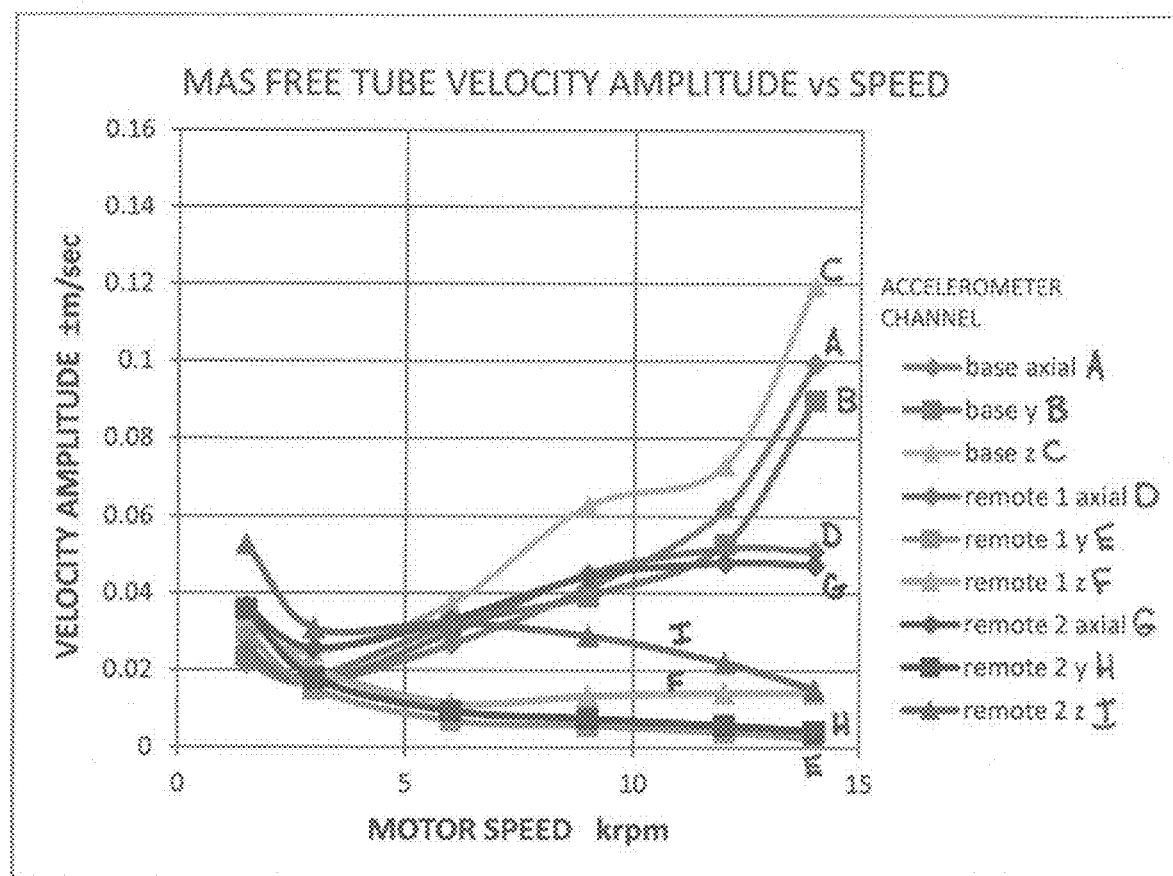
Figure 10C:
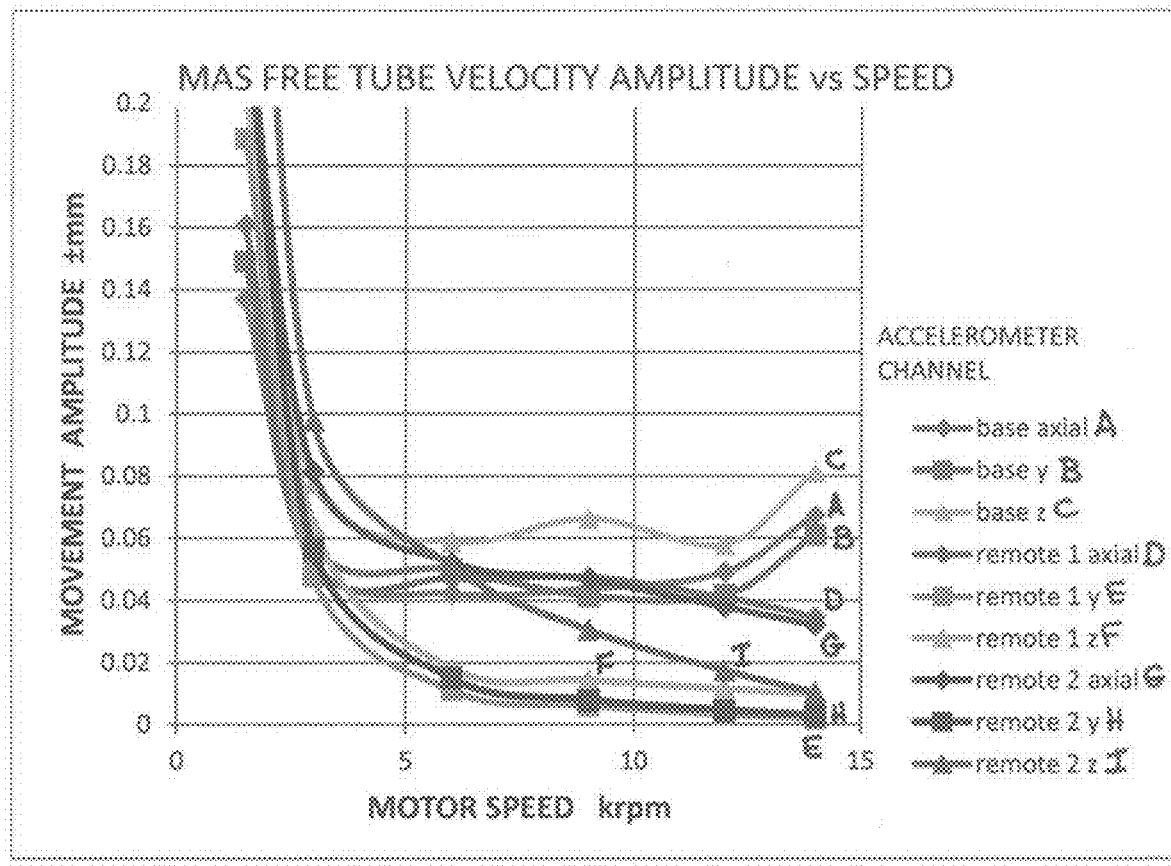

Testing the MAS device 100 in a laboratory environment also shed light on how the effectiveness of the device came about. Referring to FIGS. 10A-10C, in a test configuration, the MAS device 100 was connected to a tube 102 and accelerometers for measuring acceleration along X, Y, and Z axes were attached to the tube both at the MAS device and about 20 cm downstream. The X-axis coincides with the axis of the tube 102. The tube was left hanging vertically to mimic the typical arrangement when used as a post-operative chest cavity drainage tube. The MAS device 100 was configured with a 0.529 g eccentric weight offset 0.85 cm from the motor axis.

FIGS. 10A-C illustrate the acceleration, velocity, and movement, respectively measured via the accelerometers during operation of the test configuration. While not surprising that some values increase with motor speed, it is interesting to see that movement amplitude (FIG. 10C) remains relatively flat over the motor operating range of about 3-12 krpm. It is also important to note that, within this span, the movement amplitude was relatively consistent, both at the location of the MAS device 100 and at the remote accelerometer locations 16-20 cm downstream. This gives positive indication that the configuration of the MAS device 100 produces even consistent movement along a significant length of the tube.

Noting that it is shear stresses between the tube wall and the tube fluids that help prevent clotting, coagulation, thrombus, etc., and that shear stresses arise due to relative movement between the tube wall and the fluid column, it follows that uniform movement along the length of the tube 102 is highly desirable. Once an effective movement amplitude is determined, the MAS device 100 can be set to run at that speed, and it will create the desired tube movement along the length of the tube. Thus, viewing the results in FIG. 10C, contrary to what may be intuitive, higher motor speed does not necessarily yield better results. In fact, considering the motion in terms of frequency as opposed to rpms, the operating range of 3-12 krpm discussed above translates to 50-200 Hz (rpm/60). This further illustrates that it is tube/fluid motion, as opposed to vibration, that produces the oscillatory motion sufficient to concentrate shear stresses in a fluid boundary layer adjacent an inner wall of the tube.

From the above, it will be appreciated that certain frequency-amplitude combinations will produce the desired tube-fluid relative movement and resulting shear stresses along the desired length of the tube 102. These combinations can, of course, vary depending on the makeup of the system, the size, weight, material of the tube 102. Given, however, that the tube 102 is likely a standard size, e.g., a 32 FR chest tube draining blood from a chest cavity after open-heart surgery, an ideal frequency-amplitude combination can be determined and implemented.

Figure 11A:
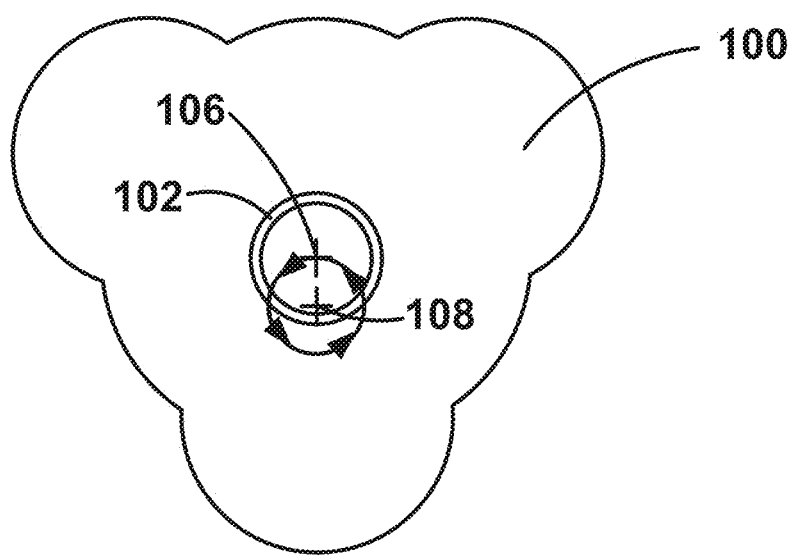
FIGS. 11A-11B are schematic illustrations depicting the operation of the device.
Figure 11B:
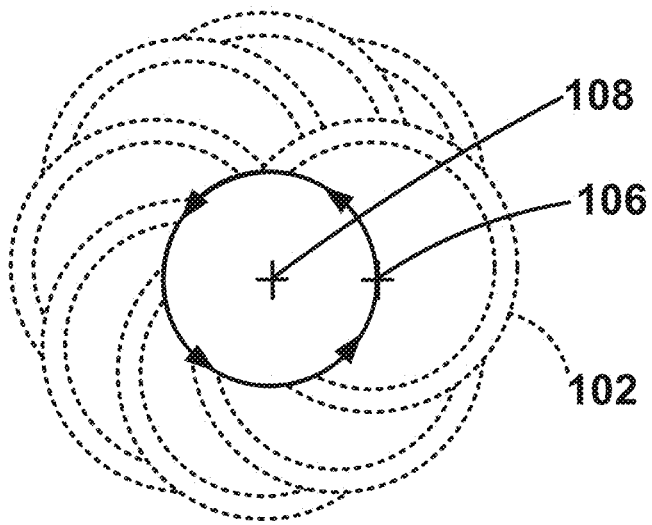

Additionally, from the above, it can be appreciated it is desirable for the shear stresses in the boundary layer adjacent the inner wall of the tube 102 to be uniform so that clotting, coagulation, thrombus, etc. can be prevented circumferentially along the length of the tube. Because the tube has a circular cross-section, it can be desirable to impart the oscillating with a motion that is as purely circular as possible. Viewing FIGS. 11A-B, the desired oscillating motion of the tube 102 is circular, i.e., the motion imparted to the tube is such that the tube axis 106 travels or orbits in a circular pattern about an oscillation axis 108.

Circular oscillating motion imparted to the tube 102 can induce or otherwise cause a swirling motion of the fluids within the tube. The swirling motion exhibits hysteresis with the oscillating motion in that it is slower and lags behind the motion of the tube 102 and the MAS device 100. The swirl can thus be indicative of 1) that the oscillating motion imparted to the tube 102 is in fact circular, and 2) the magnitude of the effect that the oscillating motion is having on the fluid in the tube and, more importantly, the shear stress being applied at the fluid boundary layer. Thus, during testing, the presence of the swirling motion was found to be indicative of the desired tube-fluid column relative movement.

Advantageously, the tri-lobular configuration of the MAS device 100 and housing 110, coupled with the distribution of the components housed within the housing, lends to the effective and efficient transfer of motion from the device to the tube 102 in a circular, oscillating manner. More specifically, the tri-lobular configuration of the MAS device 100 allows for the center of mass of the device (referred to herein as device center of mass, or "DCM," see FIGS. 4 and 5) to be positioned on or close to the central axis 104 of the device. This is because the components housed in the three lobes—the motor 140 and weight 142 in the motor lobe 130 and the batteries 200 in their respective battery lobes 180— take advantage of the fact that they can be configured to have about the same mass and weight distribution. Spacing these equivalent or approximately equivalent masses 120 degrees apart about the central axis 104 causes their combined centers of mass, as well as the DCM, to be positioned on or approximately on the central axis of the device.

This is advantageous for several reasons. First, from a mechanical perspective, placing the DCM on the device centerline 104 also places the DCM on the centerline/axis 106 of and center of mass of the tube 102. Thus, the motion of the MAS device 100 is imparted to the tube 102 as accurately and completely as possible. If the MAS device 100 undergoes a circular oscillating motion when operated, then so will the connected tube 102. This eliminates sources of error—factors that would otherwise lead to the motion applied to the tube 102 differing from the motion of the MAS device 100. For example, if the center of mass of the MAS device 100 was offset significantly from the centerline/axis 106 of the tube 102, the system (i.e., the MAS device and the tube together as a whole) would experience torque arm forces that would counter the results realized when the MAS device is connected in-line, concentrically with the tube.

For example, placing the DCM of the MAS device 100 away from the tube axis 106 could result in bending moments being applied to the tube 102. Thus, the circular oscillatory motion of the MAS device 100 could be transformed to linear bending of the tube and shaking the tube laterally which would negatively affect the generation shear stresses that prevent clotting, coagulation, thrombus, etc. Placing the DCM of the MAS device 100 away from the tube axis 106 also could tend to distort or otherwise transform the circular oscillations of the MAS device 100 to non-circular, e.g., linear or oblong motions of the tube 102 at the interface with the tube. In fact, the weight of the MAS device 100 itself would apply a bending moment to the tube, even when the device is not operating. All of these factors would negatively impact the ability of the MAS device 100 to produce the shear stresses at the fluid boundary layer adjacent the inner wall of the tube 102. Advantageously, configuring the MAS device 100 with the DCM located on the centerline 104 can prevent this by allowing the device to be suspended vertically by the tube 102 so that the weight of the device acts along the centerline 104 and does not apply any torque or bending to the tube.

Placing the DCM on the device centerline 104 also provides for a small, compact form factor for the MAS device 100. This can be advantageous because it allows the MAS device 100 to occupy a small amount of space, as close to the tube 102 as possible. In post-operative scenarios, especially those involving open-heart surgical procedures, there can be a myriad of tubes, cables, wires, etc. surrounding the patient. The small, compact form factor of the MAS device 100 is of slight intrusion and therefore can help prevent inconveniences related to accessing the patient and creating any tangles.

Because coagulation and clotting are accumulative phenomena, and because further coagulation and clotting builds on previous coagulation/clots and therefore can become exponential in growth, small improvements in anti-coagulation/clotting can have a great, exponential effect. Accordingly, the MAS device 100, being configured to place the DCM on the centerline 104, can impart efficient and effective motion to the tube 102, producing the desirable shear stress at the fluid boundary layer to help prevent clotting, coagulation, thrombus, etc.

Those skilled in the art will appreciate that the example configuration of FIGS. 4-9 is advantageously configured to place the center of mass of the MAS device 100 on the centerline 104 of the device and the tube 102. In this example configuration, this is achieved through the tri-lobular configuration of the MAS device 100. This tri-lobular configuration set forth in the example configuration is not, however, meant to be limiting. The advantages displayed in this example configuration of the MAS device 100 are owed to the placing of the center of mass of the device on or about the shared centerline 104 of the device and tube 102. These advantages can be realized by device configurations other than the example tri-lobular configuration illustrated in FIGS. 4-9.

For example, placing of the center of mass of the device on or about the shared centerline of the device and tube can be realized in any configuration including two or more lobes of equal or substantially equal mass, as long as they are spaced equally about the axis. Thus, for example, whereas the illustrated tri-lobular configuration takes on a generally triangular configuration when viewed in cross-section, a four-lobed configuration would take on a generally square configuration when viewed in cross-section, a five-lobed configuration would take on a generally pentagonal configuration when viewed in cross-section, etc.

In these example configurations, the DCM location can be maintained by maintaining the number of batteries at one less than the number of lobes, with each battery occupying a lobe and the remaining lobe being occupied by the motor and associated components. In this manner, the components (i.e., motor, weights, batteries, controller, switch, etc.) can be distributed or arranged about the longitudinal axis spaced equally both radially (i.e., radius—distance from the axis) and circumferentially (i.e., along a circumference line at that radius) in order to maintain the DCM on or about the central longitudinal axis.

Additionally, the housing need not have a lobed configuration in order to place the center of mass of the device on or about the shared centerline of the device and tube. For example, the same relative positioning of the internal components of the device (i.e., the motor, weight, batteries, etc.) can be maintained in a housing configuration that departs from the example lobed configuration. The housing configuration could, for example, be cylindrical, square/rectangular box-shaped, pentagonal, hexagonal, etc. The housing can also be configured to have an uneven weight or mass distribution in order to balance with uneven component weight/mass distribution. For example, referring to FIG. 6, the strap 146 securing the motor 140 in the housing 110 could be configured to add mass to the motor lobe 130. As another example, referring to FIG. 7, the battery compartment doors 184 could be configured to have a thickness (e.g., thinned) that reduces the mass of the battery lobes 180.

The foregoing description and examples have been set forth merely to illustrate the invention and are not intended as being limiting. Each of the disclosed aspects and embodiments of the present invention may be considered individually or in combination with other aspects, embodiments, example configurations, and variations of the invention. Further, while certain features of embodiments and example configurations of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A device for minimizing obstruction in a medical device in the form of a flexible tube for draining fluids from a patient, comprising:
   a housing defining a channel configured to receive and secure a section of the flexible tube such that the section of the flexible tube extends coaxially with a central longitudinal axis of the channel; and
   components supported in the housing and configured to be operated to impart motion to the housing and the attached flexible tube, the motion being configured to produce oscillatory motion of a frequency sufficient to concentrate shear stresses in a fluid boundary layer adjacent an inner wall of the flexible tube;
   wherein the housing and at least one of the components each have a longitudinal axis that extends generally parallel to the longitudinal axis of the channel, and wherein the housing and the components supported in the housing are configured and arranged so that a device center of mass lies along or near the longitudinal axis of the channel.

2. The device recited in claim 1, wherein the components comprise a motor and one or more batteries, wherein the one or more batteries and the motor are spaced about the longitudinal axis both radially and circumferentially to place the device center of mass along or near the longitudinal axis of the channel.

3. The device recited in claim 2, wherein the motor comprises a DC motor and the components further comprise an eccentric weight connected the motor, one or more batteries, and a controller for controlling electrical current directed to the motor from the one or more batteries in order to control the operation of the motor.

4. The device recited in claim 2, wherein the housing has a lobed configuration comprising a plurality of lobes spaced generally equally about the longitudinal axis both radially and circumferentially.

5. The device recited in claim 4, wherein one of the lobes houses the motor and the remaining lobes house the one or more batteries.

6. The device recited in claim 5, wherein the components are configured such that the mass of the components housed in each lobe is about the same.

7. The device recited in claim 6, wherein the components housed in the lobe housing the motor comprise an eccentric weight connected to the motor and a controller for controlling electrical current directed to the motor from the one or more batteries in order to control the operation of the motor.

8. The device recited in claim 4, wherein the lobes are configured to receive the components, and wherein each lobe is configured to have a mass that, when combined with the mass of the components housed in the lobe, is about equal to each of the other lobes.

9. The device recited in claim 2, wherein the motor and the one or more batteries have longitudinal axes that extend generally parallel to the longitudinal axis of the channel.

10. The device recited in claim 1, wherein the flexible tube comprises a catheter for carrying body fluids.

11. The device recited in claim 1, wherein the flexible tube comprises a chest tube for carrying body fluids.

12. The device recited in claim 1, wherein the frequency is in the range of 50-200 Hz.

13. The device recited in claim 1, wherein the oscillatory motion induces swirl in the fluids in the flexible tube.

14. A device for minimizing obstruction in a medical device in the form of a flexible tube for draining fluids from a patient, comprising:
    a housing defining a channel configured to receive and secure a section of the flexible tube such that the section of the flexible tube extends coaxially with a central longitudinal axis of the channel; and
    components supported in the housing, the components comprising a motor operable to impart motion to the housing and one or more batteries for supplying electrical energy for operating the motor, wherein the motion is configured to impart motion to the housing and the attached flexible tube, the motion being configured to produce oscillatory motion of a frequency sufficient to concentrate shear stresses in a fluid boundary layer adjacent an inner wall of the flexible tube;
    wherein the motor and each of the one or more batteries have longitudinal axes that extend generally parallel to the longitudinal axis of the channel and are spaced from each other generally equally about the longitudinal axis both radially and circumferentially.

15. The device recited in claim 14, wherein the frequency is in the range of 50-200 Hz.

16. The device recited in claim 14, wherein the oscillatory motion induces swirl in the fluids in the flexible tube.

17. The device recited in claim 14, wherein the housing has a lobed configuration comprising a lobe for receiving the motor and components associated with the motor, and a lobe for receiving each of the one or more batteries and the components associated with the one or more batteries, wherein the lobes are spaced from each other generally equally about the longitudinal axis both radially and circumferentially.

18. A device for minimizing obstruction in a medical device in the form of a flexible tube for draining fluids from a patient, comprising:
    a housing defining a channel configured to receive and secure a section of the flexible tube such that the section of the flexible tube extends coaxially with a central longitudinal axis of the channel;
    a motor operable to impart motion to the housing and one or more batteries for supplying electrical energy for operating the motor;
    wherein the housing has a lobed configuration comprising a lobe for receiving the motor and components associated with the motor, and a lobe for receiving each of the one or more batteries and the components associated with the one or more batteries;

wherein the lobes extend generally parallel to the longitudinal axis of the channel and are spaced from each other generally equally about the longitudinal axis of the channel both radially and circumferentially.

19. The device recited in claim 18, wherein the motion imparted to the housing imparts motion to the attached flexible tube, the motion being configured to produce oscillatory motion of a frequency sufficient to concentrate shear stresses in a fluid boundary layer adjacent an inner wall of the flexible tube.

20. The device recited in claim 19, wherein the oscillatory motion induces swirl in the fluids in the flexible tube.

21. The device recited in claim 18, wherein the motion imparted by the motor is at a frequency in the range of 50-200 Hz.

* * * * *